United States Patent
Bornefalk et al.

(10) Patent No.: US 11,246,559 B2
(45) Date of Patent: Feb. 15, 2022

(54) CALIBRATION OF AN X-RAY IMAGING SYSTEM

(71) Applicant: Prismatic Sensors AB, Stockholm (SE)

(72) Inventors: Hans Bornefalk, Vallentuna (SE); Fredrik Grönberg, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 138 days.

(21) Appl. No.: 16/774,594

(22) Filed: Jan. 28, 2020

(65) Prior Publication Data
US 2020/0261050 A1    Aug. 20, 2020

Related U.S. Application Data

(60) Provisional application No. 62/805,533, filed on Feb. 14, 2019.

(51) Int. Cl.
A61B 6/00 (2006.01)
G06T 11/00 (2006.01)
A61B 6/03 (2006.01)

(52) U.S. Cl.
CPC .............. *A61B 6/584* (2013.01); *A61B 6/032* (2013.01); *A61B 6/585* (2013.01); *G06T 11/005* (2013.01)

(58) Field of Classification Search
CPC ......... A61B 6/584; A61B 6/032; A61B 6/585; G06T 11/005
See application file for complete search history.

(56) References Cited

U.S. PATENT DOCUMENTS

| 4,724,110 A | * | 2/1988 | Arnold | G09B 23/28 264/102 |
| 5,178,146 A | * | 1/1993 | Giese | G01R 33/58 324/308 |

(Continued)

FOREIGN PATENT DOCUMENTS

| EP | 1475039 A2 | 11/2004 |
| EP | 2 865 334 A1 | 4/2015 |

(Continued)

OTHER PUBLICATIONS

Ehn et al.; Basis material decomposition in spectral CT using a semi-empirical, polychromatic adaption of the Beer-Lambert model; Physics in Medicine & Biology; Dec. 13, 2016; pp. N1-N17; vol. 62, No. 1.

(Continued)

*Primary Examiner* — David P Porta
*Assistant Examiner* — Djura Malevic
(74) *Attorney, Agent, or Firm* — Nixon & Vanderhye

(57) ABSTRACT

Disclosed is a calibration phantom for an x-ray imaging system having an x-ray source and an x-ray detector. The calibration phantom includes a combination of geometric objects of at least three different types and/or compositions including: a first object located in the middle, including a first material; a plurality of second objects arranged around the periphery of the first object, at least a subset of the second objects including a second material different than the first material, wherein the first object is relatively larger than the second objects; a plurality of third objects arranged around the periphery of the first object and/or around the periphery of at least a subset of the second objects, at least a subset of the third objects including a third material different than the first material and the second material, (Continued)

wherein the third objects are relatively smaller than the second objects.

24 Claims, 12 Drawing Sheets

(56) References Cited

U.S. PATENT DOCUMENTS

| | | | |
|---|---|---|---|
| 5,235,628 A | 8/1993 | Kalender | |
| 6,364,529 B1* | 4/2002 | Dawson | A61B 6/583 378/18 |
| 6,409,383 B1* | 6/2002 | Wang | G01T 1/169 378/204 |
| 6,419,680 B1* | 7/2002 | Cosman | G06T 3/4061 378/162 |
| 6,694,047 B1* | 2/2004 | Farrokhnia | A61B 6/583 378/163 |
| 7,056,018 B2* | 6/2006 | Stierstorfer | A61B 6/583 378/18 |
| 7,149,277 B2* | 12/2006 | Tanigawa | A61B 6/583 378/18 |
| 7,339,159 B2* | 3/2008 | Juh | A61B 6/037 250/252.1 |
| 7,642,506 B2* | 1/2010 | Wang | A61B 6/583 250/252.1 |
| 7,738,624 B2* | 6/2010 | Herold | A61B 6/032 378/18 |
| 8,121,250 B2* | 2/2012 | Dafni | A61B 6/032 378/18 |
| 8,309,910 B2* | 11/2012 | Dutta | A61B 6/583 250/252.1 |
| 8,644,906 B2* | 2/2014 | Piferi | A61B 90/39 600/414 |
| 8,708,562 B1* | 4/2014 | Nosil | A61B 6/583 378/207 |
| 8,764,290 B2* | 7/2014 | O'Hare | A61B 6/583 378/207 |
| 9,420,983 B2 | 8/2016 | Zagorchev et al. | |
| 9,681,851 B2* | 6/2017 | Rohler | A61B 6/542 |
| 9,750,479 B2* | 9/2017 | Singh | A61B 6/582 |
| 9,761,022 B1* | 9/2017 | Gronberg | A61B 6/583 |
| 9,936,935 B1* | 4/2018 | Nosil | G01T 1/169 |
| 10,197,654 B2* | 2/2019 | Takayama | A61B 6/4417 |
| 10,357,221 B2* | 7/2019 | Bechwati | A61B 6/032 |
| 10,492,755 B2* | 12/2019 | Lin | A61B 6/461 |
| 10,585,051 B2* | 3/2020 | O'Hare | G01B 3/30 |
| 10,660,600 B2* | 5/2020 | Avila | G01T 7/005 |
| 10,702,237 B2* | 7/2020 | Kirby | A61B 6/58 |
| 10,835,765 B2* | 11/2020 | Tulik | A61N 5/1081 |
| 2003/0072409 A1* | 4/2003 | Kaufhold | A61B 5/4869 378/53 |
| 2008/0093544 A1* | 4/2008 | Wang | A61B 6/583 250/252.1 |
| 2009/0190723 A1 | 7/2009 | Jang et al. | |
| 2010/0131885 A1* | 5/2010 | Licato | A61B 6/482 715/781 |
| 2011/0200244 A1* | 8/2011 | Ashton | G06T 11/008 382/131 |
| 2011/0257919 A1* | 10/2011 | Reiner | G16H 30/20 702/81 |
| 2012/0076259 A1 | 3/2012 | Holt | |
| 2012/0155617 A1* | 6/2012 | Dutta | A61B 6/583 378/207 |
| 2014/0153694 A1 | 6/2014 | Suppes et al. | |
| 2015/0223906 A1* | 8/2015 | O'Neill | A61B 6/0492 600/407 |
| 2015/0282781 A1* | 10/2015 | Rohler | A61B 6/545 378/207 |
| 2018/0035970 A1* | 2/2018 | Avila | G01T 7/005 |
| 2018/0249983 A1 | 9/2018 | Daerr et al. | |

FOREIGN PATENT DOCUMENTS

| | | |
|---|---|---|
| GB | 2504258 A | 1/2014 |
| WO | 2016/168292 A1 | 10/2016 |
| WO | 2017/089368 A1 | 6/2017 |

OTHER PUBLICATIONS

Alvarez; Estimator for photon counting energy selective x-ray imaging with multibin pulse height analysis; Med. Phys.; Apr. 25, 2011; pp. 2324-2334; vol. 38, No. 5.
International Search Report for PCT/SE2020/1050068 dated Mar. 23, 2020, 5 pages.
International preliminary report on patentability (Chapter I) for PCT/SE2020/1050068 dated Aug. 10, 2021, 6 pages.

* cited by examiner

CALIBRATION OF AN X-RAY IMAGING SYSTEM

The project leading to this application has received funding from the European Union's Horizon 2020 research and innovation programme under grant agreement No 830294.

TECHNICAL FIELD

The proposed technology generally relates to x-ray imaging, and more particularly to a calibration of x-ray imaging systems, including calibration phantoms and corresponding calibration procedures.

BACKGROUND

There is a general need for improved calibration of x-ray imaging systems to enable enhanced image reconstruction.

For example, there is a need for calibration of so-called Photon-Counting Spectral Computed Tomography (PCSCT) systems to be able to perform accurate material basis decomposition in the projection domain. PCSCT systems concern CT systems based on spectral (i.e. energy-discriminating) information from a photon-counting x-ray detector. This means that not only does the system respond to the counted number of individual photons, but also the energy of these individual photons is taken into account.

In this context, calibration is normally understood as a mapping between different x-ray spectra falling on a detector and the corresponding detector output. The, at least intermediate, output of a PCSCT system includes x-ray counts allocated in energy bins, typically stored as values in an n-dimensional vector (in a later processing stage these counts could be processed with a log-function). The photon-counting x-ray detector in such a system is often referred to as a photon-counting multi-bin detector. Assuming the x-ray anode is fed by constant voltage and current, and the beam filter is never changed, the difference in spectrum observed by the detector depends on what materials and thicknesses have been in the x-ray path. For example, for a 5-bin system, an example calibration mapping between some varying thicknesses of polyethylene (PE) and poly-vinyl-chloride (PVC) might look like this:

| PE thickness (cm) | PVC thickness (cm) | Average counts in each of 5 bins |
| --- | --- | --- |
| 0 | 0 | 35, 47, 100, 36, 14 |
| 10 | 0 | 14, 23, 67, 18, 7 |
| 10 | 2 | 9, 18, 45, 15, 5 |
| 0 | 2 | 28, 35, 80, 23, 12 |
| Etc | | |

Material basis decomposition in the projection domain is the process to determine the equivalent pathlength in centimetres of some reference materials, typically two or three, that the x-ray photons of an exposure have passed through. This is typically achieved by some type of inversion of the calibration data or a model of the calibration data. Note that during calibration, several exposures of a stationary phantom can be acquired. The result will be close to noise-less data. When applied to individual projections, for example when constructing an image of a dose sensitive human patient, the limited dose and resulting Poisson noise will make the inversion problem more difficult.

Practical Considerations

There are two major practical concerns when constructing a calibration phantom for use in an x-ray imaging system such as a clinical PCSCT system. The first is that a large-enough part of the material-space has to be sampled (all combinations of PE and PVC above, or some other combination of clinically relevant materials) for each of the detector elements of the system. The second is that this must be possible to perform in practice.

A typical conventional approach to sampling a large-enough part of the material space for prototype systems is to use a step-wedge phantom with different pathlength combinations as illustrated schematically in FIG. 1.

FIG. 1 is a schematic diagram illustrating an example of a simple two-material step wedge phantom with 5×5 material combinations. As the phantom is scanned in the z-direction, each detector line sees a known material combination. The line tilted at $\tau$ radians illustrates an x-ray beam hitting a finite detector element. All detector elements (or rows of detector elements) in the z-direction can be exposed at the same time, but only one beam hitting one detector element is shown. It is important to avoid partial volume effects (i.e. part of the beam in the direction perpendicular to the x-ray motion passing through different material combinations).

The simple concept of planar step wedge phantoms is not easily extended to multi-slice systems with large z-coverage for a multitude of reasons. Here we will briefly mention three: 1) size, affecting handling and manufacturing cost, 2) the required accuracy of placement, and 3) scatter profiles.

To avoid partial volume effects as the phantom is stepped in the z-direction, the entire extent of the beam hitting a detector must lie within a single material combination. For wide coverage detectors, with 8 cm coverage in the iso-center and a typical source-to-iso distance of 50 cm, the cone angles $\tau$ range from −0.08 to 0.08 radians. Even if a margin for the placement of the phantom is not considered, which could also result in partial volume measurement and thus corrupt calibration data, the length of the step would have to be at least the detector element size+L2×tan $\tau_{max}$. For L2=2 cm and a pixel width in the z-direction of 0.5 mm in iso-center, this indicates that the step size in a step wedge phantom has to be at least 0.21 cm. Adding a small margin yields 0.25 cm per step. Even for a small 3-material phantom with 6 different pathlengths of each material the extent of the step wedge in the z-direction quickly becomes very large, 6*6*6*0.25 cm=54 cm. Since one ideally wants to sample even more material combinations, it is clear that the step wedge approach quickly becomes unattractive from a weight and cost perspective.

A step wedge furthermore places strict requirements on positioning of the phantom. If the phantom is allowed to be somewhat tilted in the z-direction, added margin and larger step sizes are needed to avoid partial volume effects (as the tilt angle would add to the cone angle in the tan $\tau$-factor.

Finally, the strong non-homogeneity of the phantom in the z-direction would result in an unequal amount of scattered radiation hitting each detector element from the positive and negative z-directions. This would not be representative of imaging a real object.

It should be understood that there is a lot of general prior art on phantoms for CT, but most of them are focused on either Quality Control (QC), geometric calibration or the optimization of beam hardening correction methods. There is also a group of phantoms intended for use in the system simultaneously with the patient, for example U.S. Pat. No.

9,420,983B1, intended to improve tissue characterization by comparison with real-time data from known materials.

None of these are designed to generate a mapping between different x-ray spectra falling on a detector and e.g. the corresponding x-ray counts allocated in energy bins for subsequent use in material basis decomposition.

Just for a more complete understanding, QC testing of CT scanners typically includes measurement of CT numbers in a reconstructed image of a CT phantom using a standardized protocol. CT number values are normally expressed in terms of Hounsfield Units (HU), and they are clinically relevant in determining the composition of various tissues in the body. Effective quality control requires that tolerance ranges of CT/HU values are defined: a measured value outside the range indicates the need for further investigation and possible recalibration of the scanner. Normally, the measurement results are used to define manufacturer- and kVp-specific tolerance ranges for the CT numbers of each material in the phantom. Quality control phantoms are supplied to the users by the vendors and by independent third-party suppliers. Other uses of QC phantoms include ensuring that the geometry of acquisition system is correctly determined (otherwise artefact will occur) as for example WO 2016/168292A1.

Calibration phantoms for the determination of detector-element specific beam hardening or scatter correction schemes include EP1475039B1, U.S. Pat. No. 7,056,018B2 and U.S. Pat. No. 8,121,250B2. A common feature of these technical solutions is that the phantom is either large enough to cover the entire radiation field or is shifted around at multiple positions to cover a multitude of different path-length. Typically, the phantoms consist of a single piece of a homogenous material (with attenuation properties similar to water), but solutions with different materials and multiple pieces have been proposed (U.S. Pat. No. 8,121,250B2). Also, typically the placement of the phantom needs to be very precise, although solutions where placement insensitivity is achieved by using the x-ray data to determine the actual location have been proposed (U.S. Pat. No. 8,121,250B2).

However, none of the methods or phantoms are optimized for generating an optimal mapping between material pathlengths and attenuation data necessary for photon counting system designed to perform material basis decomposition in the projection domain. For example, U.S. Pat. No. 8,121,250B2 focuses on generating calibration corrections for beam hardening and scatter. None of the mentioned patent references focus specifically on phantoms or methods specifically tailored to the need of photon counting x-ray imaging systems, e.g. intended to perform material basis decomposition in the projection domain.

There is thus a general need for improved calibration phantoms and procedures for x-ray imaging systems such as photon-counting spectral x-ray imaging systems.

SUMMARY

It is a general object to provide an improved calibration phantom for x-ray imaging systems.

It is also an object to provide an improved calibration procedure for x-ray imaging systems.

It is a specific object to provide a calibration phantom for an x-ray imaging system.

It is another object to provide a method for calibration of an x-ray imaging system.

These and other objects may be achieved by one or more embodiments of the proposed technology.

According to a first aspect, there is provided a calibration phantom for an x-ray imaging system having an x-ray source and an x-ray detector. The calibration phantom comprises a combination of geometric objects of at least three different types and/or compositions including:
  a first object located in the middle, comprising a first material;
  a plurality of second objects arranged around the periphery of the first object, at least a subset of the second objects comprising a second material different than the first material, wherein the first object is relatively larger than the second objects;
  a plurality of third objects arranged around the periphery of the first object and/or around the periphery of at least a subset of the second objects, at least a subset of the third objects comprising a third material different than the first material and the second material, wherein the third objects are relatively smaller than the second objects.

According to a second aspect, there is provided a method for calibration of an x-ray imaging system having an x-ray source and an x-ray detector. The method comprises:
  placing a calibration phantom according to the first aspect in the beam path of the x-ray imaging system;
  turning on the x-ray source and beginning a calibration sequence based on controlled movement of the calibration phantom;
  acquiring projection data for a set of projections based on the output of the x-ray detector;
  determining path lengths through the different materials of the calibration phantom for each of the projections; and
  generating a mapping between the path lengths and detector response of the x-ray detector.

In this way, it is possible to calibrate an x-ray imaging system such as a photon-counting spectral CT system to allow it to perform improved and/or artefact-free material basis decomposition and/or image reconstruction.

The present invention addresses at least some of the issues with the prior art solutions by a unique phantom that is not highly sensitive to erroneous placement. The novel phantom does not have to change shape in the z-direction, thereby minimizing any potential bias introduced by uneven scattered radiation.

BRIEF DESCRIPTION OF DRAWINGS

The embodiments, together with further objects and advantages thereof, may best be understood by making reference to the following description taken together with the accompanying drawings, in which.

DETAILED DESCRIPTION

A basic idea is to provide a calibration phantom for an x-ray imaging system having an x-ray source and an x-ray detector, where the calibration phantom comprises a combination of geometric objects of at least three different types and/or compositions including:
 a first object located in the middle, comprising a first material;
 a plurality of second objects arranged around the periphery of the first object, at least a subset of the second objects comprising a second material different than the first material, wherein the first object is relatively larger than the second objects;
 a plurality of third objects arranged around the periphery of the first object and/or around the periphery of at least a subset of the second objects, at least a subset of the third objects comprising a third material different than the first material and the second material, wherein the third objects are relatively smaller than the second objects.

It should be understood that the term "periphery" normally refers to and/or corresponds to the outside boundary, outside parts and/or outside surface of an object.

By way of example, at least a subset of the third objects may be arranged around the periphery of the first object in-between at least a subset of the second objects.

Figure 1:
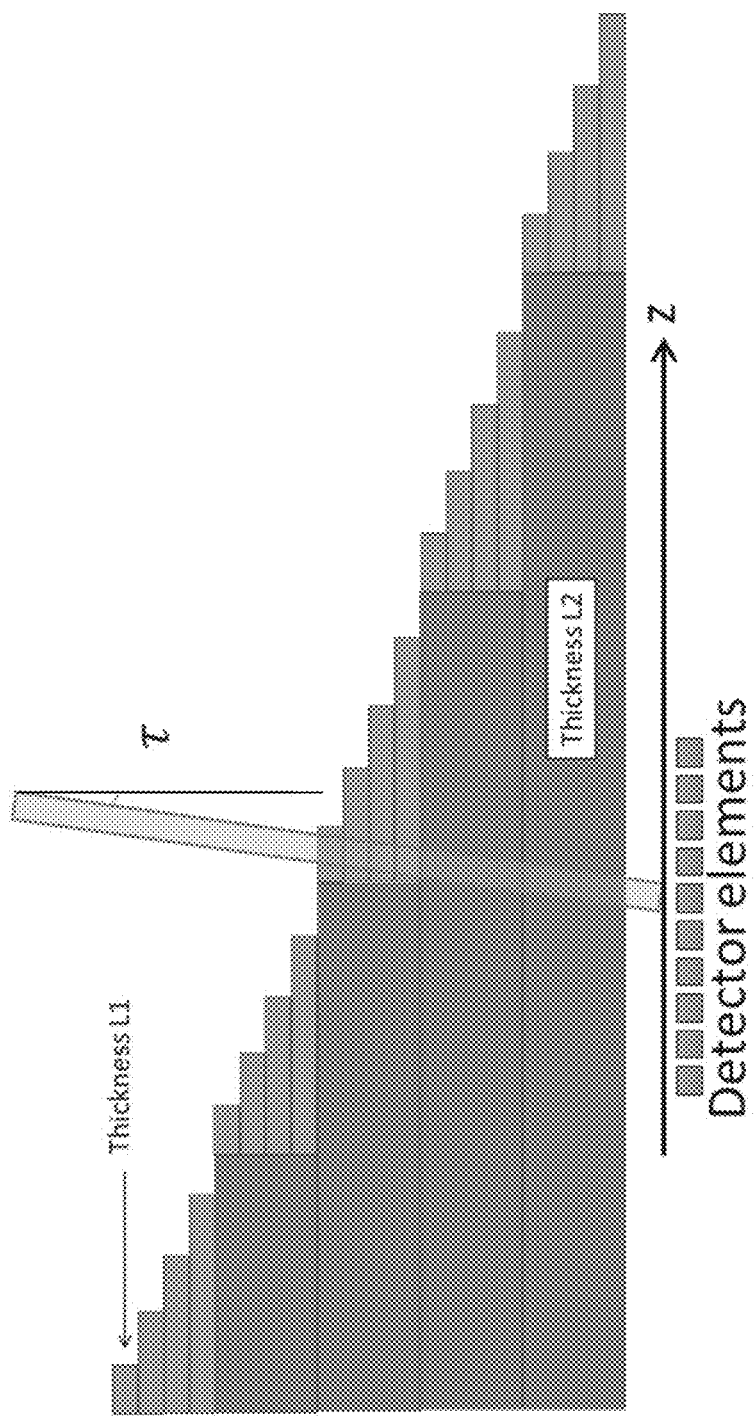
FIG. 1 is a schematic diagram illustrating an example of a simple two-material step wedge phantom with 5×5 material combinations.
Figure 2:
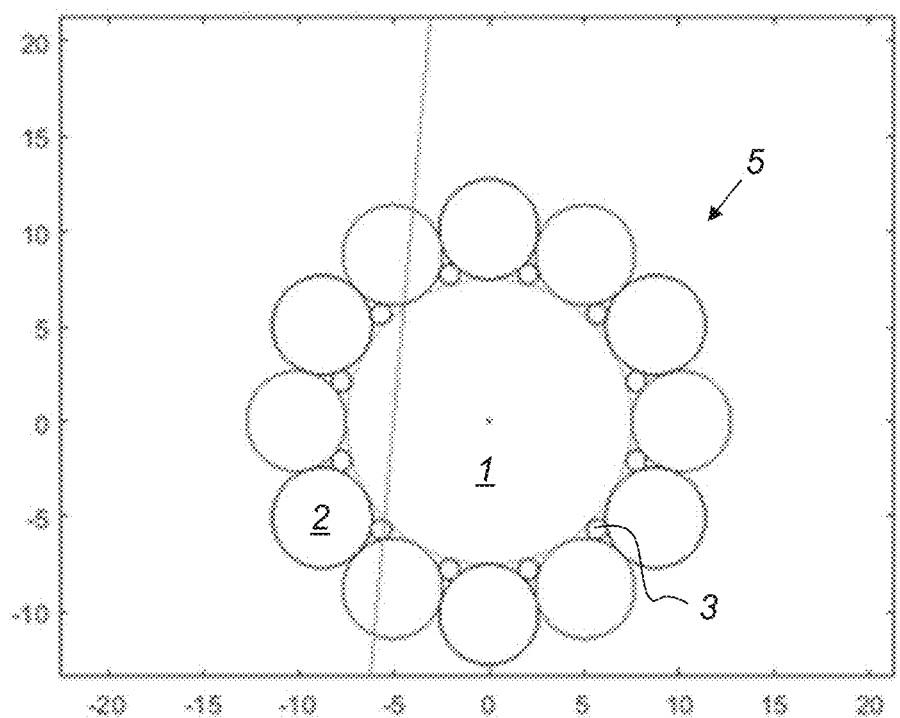
FIG. 2 is a schematic diagram illustrating a cross-section of a non-limiting example of a calibration phantom according to an embodiment.

FIG. 2 is a schematic diagram that illustrates a cross section view of a non-limiting example of a specific case of such a phantom configuration 5, exemplified with cylinders 1, 2, 3 of three different sizes and materials. The line through the phantom indicates the path of a particular x-ray projection, being the straight line that connects the x-ray focal spot and a specific detector element.

Figure 3:
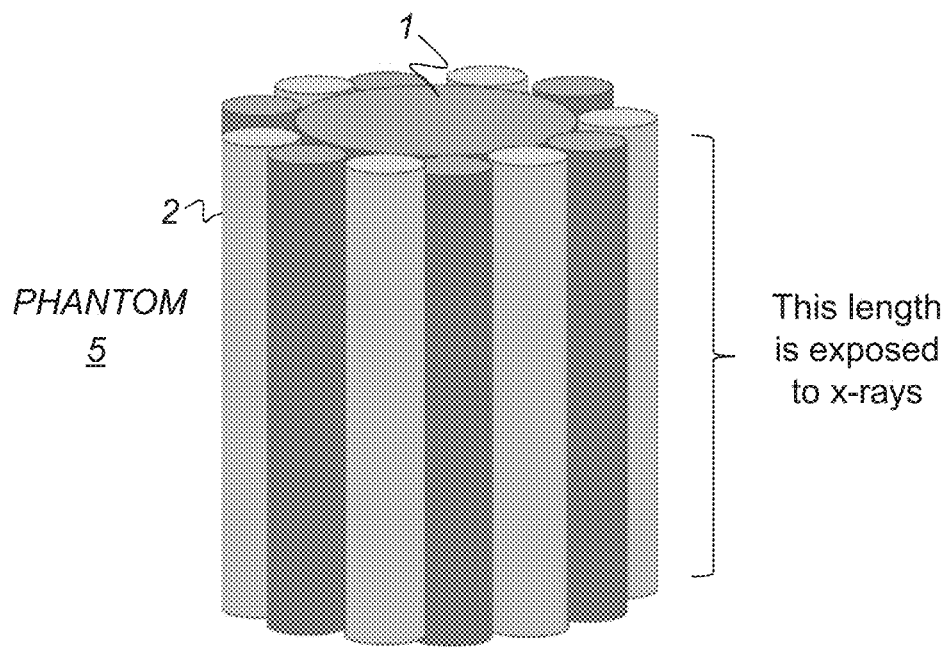
FIG. 3 is a schematic diagram illustrating a three-dimensional view of a non-limiting example of a calibration phantom according to an embodiment.

FIG. 3 is a schematic diagram illustrating a corresponding three-dimensional view of a non-limiting example of a calibration phantom 5 according to an embodiment. The third small objects (e.g. rods or cylinders) cannot be seen in this view, just the first object 1 and the second objects 2.

It should though be understood that the third objects or a subset thereof may be arranged around the periphery of at least a subset of the second objects, without being in contact with the first object, e.g. placed on the outer bound of the overall structure and not placed in-between the first object and the second objects.

It should also be understood that the objects do not have to be cylinders or rods, as illustrated in the particular examples of FIG. 2 and FIG. 3, but can in fact be any physical objects suitable for use in a calibration phantom. For example, the first object, the second objects and the third objects may be elongated objects extending in a direction substantially perpendicular to the intended x-ray direction and/or extending in the scanning direction.

Figure 14:
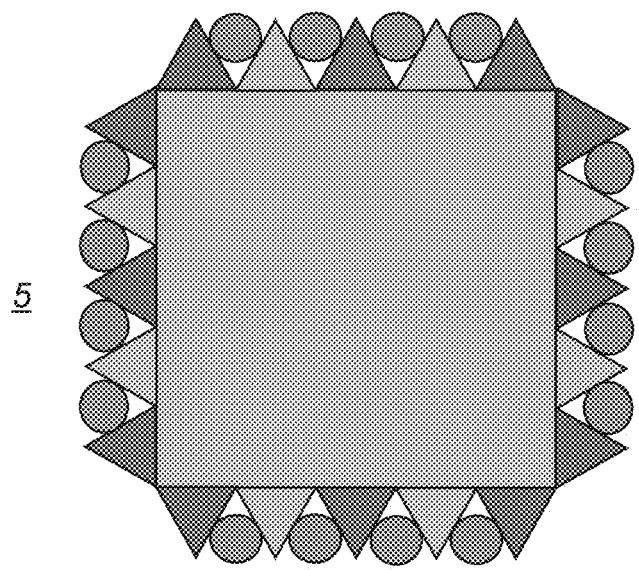
FIG. 14 is a schematic diagram illustrating a cross-section of another non-limiting example of a calibration phantom according to an embodiment.

By way of example, the first object, the second objects and the third objects may include at least one of cylinders, cuboids, and prisms (see also FIG. 14).

In a particular example, as illustrated in FIG. 2 and FIG. 3, the first object is a middle cylinder 1, the second objects are medium-sized cylinders 2 spaced around the periphery of the middle cylinder 1, and the third objects 3 are smaller cylinders arranged around the periphery of the middle cylinder 1 and/or around the periphery of at least a subset of the medium-sized cylinders 2.

It should be understood that the term "cylinder" includes a circular cylinder, elliptical cylinder and/or any other type of cylinder.

For example, at least a subset of the smaller cylinders 3 may be arranged around the periphery of the middle cylinder 1 in spacings in-between at least a subset of the medium-sized cylinders 2, e.g. as schematically illustrated in FIG. 2.

Preferably, the middle cylinder 1 has a larger diameter than the medium-sized cylinders 2, and the medium-sized cylinders 2 have a larger diameter than the smaller cylinders 3.

As an example, the plurality of second objects may all be of the same second material.

Alternatively, the plurality of second objects may include at least two types of second objects, of different materials and/or different sizes.

For example, a first subset of the second objects may be made of the second different material and a second subset of the second objects may be made of a different material such as the first material, e.g. as schematically illustrated in FIG. 3 as well as in FIG. 14.

It is also possible to select the size and number of the second objects so as to achieve a snug fit of the second objects around the periphery of the first object.

FIG. 14 is a schematic diagram illustrating a cross-section of another non-limiting example of a calibration phantom according to an embodiment. In this example, the first object has a rectangular or quadratic cross-section corresponding to an elongated cuboid, the second type of objects has a triangular cross-section corresponding to a triangular prism, and the third type of objects has a circular cross-section corresponding to rod or cylinder.

When it comes to material choices, the first material may be selected to mimic soft human tissue, and the second material may have a higher attenuation than the first material.

In a particular example, the first material mimics soft human tissue, the second material mimics bone, and the third material mimics a contrast agent.

As an example, the first material may comprise polyethylene (PE), and the second material may comprise poly-vinyl-chloride (PVC) or other plastic or resin.

Optionally, the calibration phantom is intended for use in a Computed Tomography (CT) system with a photon-counting multi-bin x-ray detector to enable calibration for material basis decomposition.

In a photon-counting multi-bin detector, each registered photon generates a current pulse which is compared to a set of thresholds, thereby counting the number of photons incident in each of a number of energy bins.

By way of example, the calibration phantom may be intended for use in the CT system to enable calibration for accurate material basis decomposition based on mapping between i) path length determinations through each of the first, second and third materials for each of a number of rotation angles of the CT system and each of a number of detector elements of the x-ray detector and ii) corresponding detector responses of the photon-counting multi-bin x-ray detector.

In this context, the x-ray source and the x-ray detector may be arranged on a support that is able to rotate around a subject or object to enable x-ray exposure at a set of projections at different view or rotation angles.

For a better understanding, the proposed technology will now be described in more detail with reference to non-limiting examples.

Reference can once again be made to FIG. 2, which shows a non-limiting example of a basic design or layout. In this particular example, the phantom 5 includes cylinders 1, 2, 3 of three different types and/or compositions. There is a larger middle cylinder 1, typically with ~25 cm diameter and of a material that mimics soft human tissue (polyethylene is one possibility). Spaced around the larger middle cylinder 1 are medium-sized cylinders 2, the diameter and number of which is selected, e.g. to achieve a snug fit without any substantial gaps. In a particular example, e.g. as schematically illustrated in FIG. 3, every second medium-sized cylinder 2 is made of the same material as the middle one 1, and every other second medium-sized cylinder 2 is made of a material with somewhat higher attenuation, for instance PVC or some other plastic or resin to mimic bone. This choice is merely illustrative. All medium-sized cylinders 2 can be of the same materials. There can also be more than two types of medium-sized cylinders 2 and the number with each material can differ. As an example, smaller rods or cylinders 3 may be arranged around the larger middle cylinder 1 in the spacing in-between the medium-sized cylinders 2. These smaller rods 3 may include iodine or some other contrast agent of interest. It is clear that these rods can also be fit snugly in the peripheral gap between medium-sized cylinders 2. The number of medium-sized cylinders 2 is selected to optimize the performance of the phantom in its intended use; e.g. to calibrate an x-ray imaging system such as a PCSCT system to allow it to perform artefact-free material basis decomposition and/or image reconstruction.

By way of example, the calibration phantom 5 may be constant in the scan direction, meaning all slices of the system see the same attenuation profile, with the exception of a possible correction based on the cone angle of the slice.

The reason for placing the medium-sized cylinders 2 and small-sized cylinders 3 at the periphery or outer bound of the phantom is to obtain a larger sample space of the material combinations.

If small rods with different materials are inserted in the interior part of the phantom, for instance following US20120155617A1, pathlengths of the material constituting the small rods (typically mimicking iodine) will only be seen in combination with relatively long pathlengths of the surrounding material. This is not beneficial from a basis decomposition or image reconstruction point of view.

For material basis decomposition in the projection domain, the inventors have recognized that it is beneficial to obtain more variable attenuation data (for instance combinations of iodine will very little PE or PVC). Therefore, the inventors proposed the novel, unique design of the calibration phantom as claimed herein.

During calibration, the x-ray source and detector may rotate like during a regular scan, possibly with more revolutions at each location to gather more statistics. Each detector element will see different pathlength combinations of the first, second and/or third materials at different view or rotation angles.

Benefits of the Novel Phantom Design May Include One or More of the Following:

- The phantom is easy to manufacture; just straight rods or similar geometric objects of e.g. plastic materials are needed (with prescribed sizes). For example, if rod diameters are selected appropriately, the pieces will fit snugly to each other. There is no need cast or glue them together. Only the middle part of the cylinder is in the beam path making the fixation of the rods possible outside the x-ray exposed area. Even the simplest method of holding the rods together (rubber band or adhesive tape) is acceptable, although a more complex solution is foreseen. For example, the rods or similar geometric objects may be fixed to opposite end plates, one at each end of the rods.
- The phantom only needs to cover the actual extent of the detector in the z-direction, thus making it smaller than a corresponding step wedge would be.
- More material combinations are sampled during rotation than would be possible to obtain with a step wedge.
- The phantom may be designed to be homogenous in the z-direction, thereby there will be no gradient in the scatter profile along the z-direction (an equal, and representative for a patient, amount of scatter will hit the detector from each z-direction).
- The exact position of the phantom can optionally be determined from a reconstructed image or the CT sinogram by a fitting procedure. This makes the positioning of the calibration phantom during calibration scan insensitive to rotations, translation (left-right and up-down) and most importantly tilt and skew.
- Once the position of the phantom has been determined from the fitting procedure, the pathlength through each of the three materials for each ray can be easily determined (e.g., based on the geometry illustrated in FIG. 2, a mathematical expression for the pathlength through each of the different cylinder types can be readily determined).

Figure 4B:
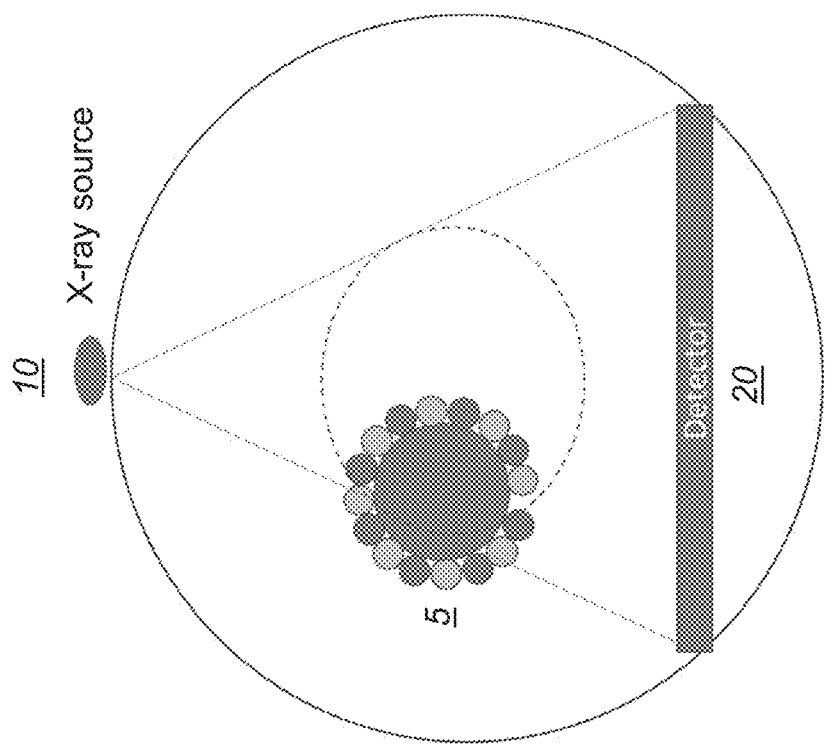
FIGS. 4A-B are schematic diagrams illustrating how the phantom can be moved towards the periphery of the field-of-view, allowing edge detector elements to see varying pathlengths for different rotation angles.
Figure 4A:
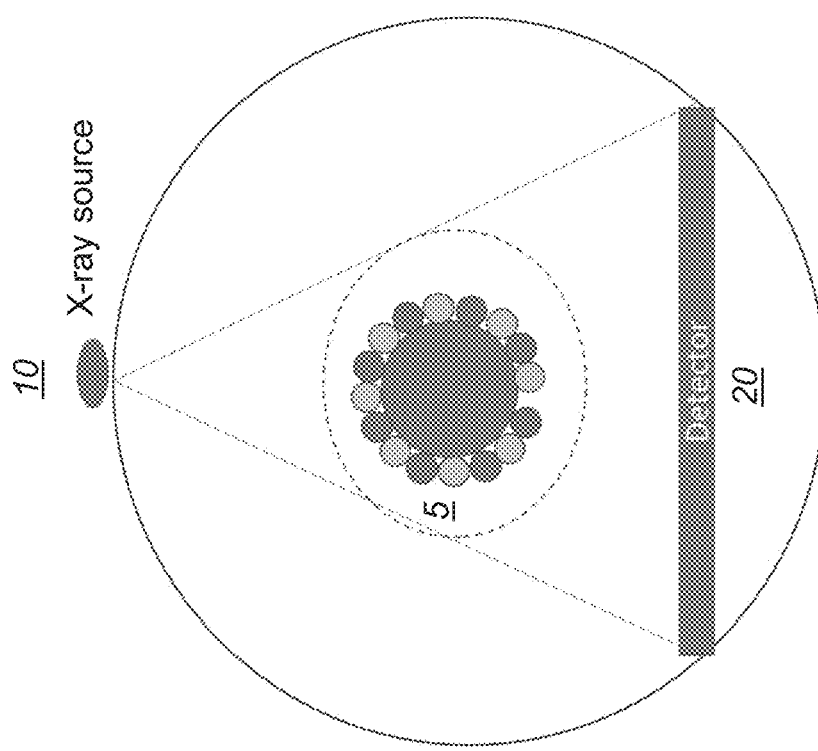

FIGS. 4A-B are schematic diagrams illustrating how the phantom 5 can be moved towards the periphery of the field-of-view, allowing edge detector elements to see varying pathlengths for different rotation angles.

If the phantom 5 is smaller than the full field of view, edge detectors will only see air should the phantom be placed only in the iso-center, as schematically illustrated in FIG. 4A. To handle this, the built-in couch movement of CT-system or some other mechanism may be used to shift the phantom 5, either up-down or left-right, as schematically illustrated in FIG. 4B.

In the example of FIG. 4A, the phantom 5 is placed in iso-center. Detector elements at the edge will not be hit by x-rays for any rotation angle. By stepping the phantom 5 towards the periphery of the field-of-view (illustrated by the dashed circle), as illustrated in FIG. 4B, detector elements at the edge will also see varying pathlengths for different rotation angles.

Figure 5:
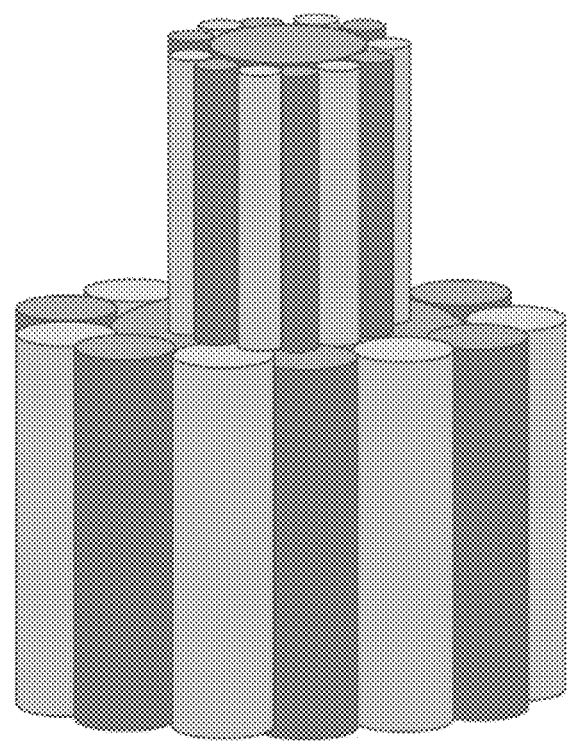
FIG. 5 is a schematic diagram illustrating an example of a combined phantom configuration useful for sampling pathlengths indicative of smaller objects.

It is clear that a smaller but similar phantom can be placed on top of the first one (or used independently) to more accurately sample the material space for combinations that occur in imaging tasks of smaller objects (infants, heads etc) as schematically illustrated in FIG. 5. To sample pathlengths indicative of head or infant scans a phantom with a smaller inner cylinder can be used. It can be attached to the first one for easier handling.

As a final example we show how the space of material pathlengths may be sampled using the phantom. For a central cylinder of 25 cm in cm, having 20 medium and small sized cylinders placed around it, and moved imaged at 11 different positions (in iso-center and 10 steps out to a maximal offset of 20 cm), the resulting pathlength combinations are shown in FIG. 6.

Figure 6:
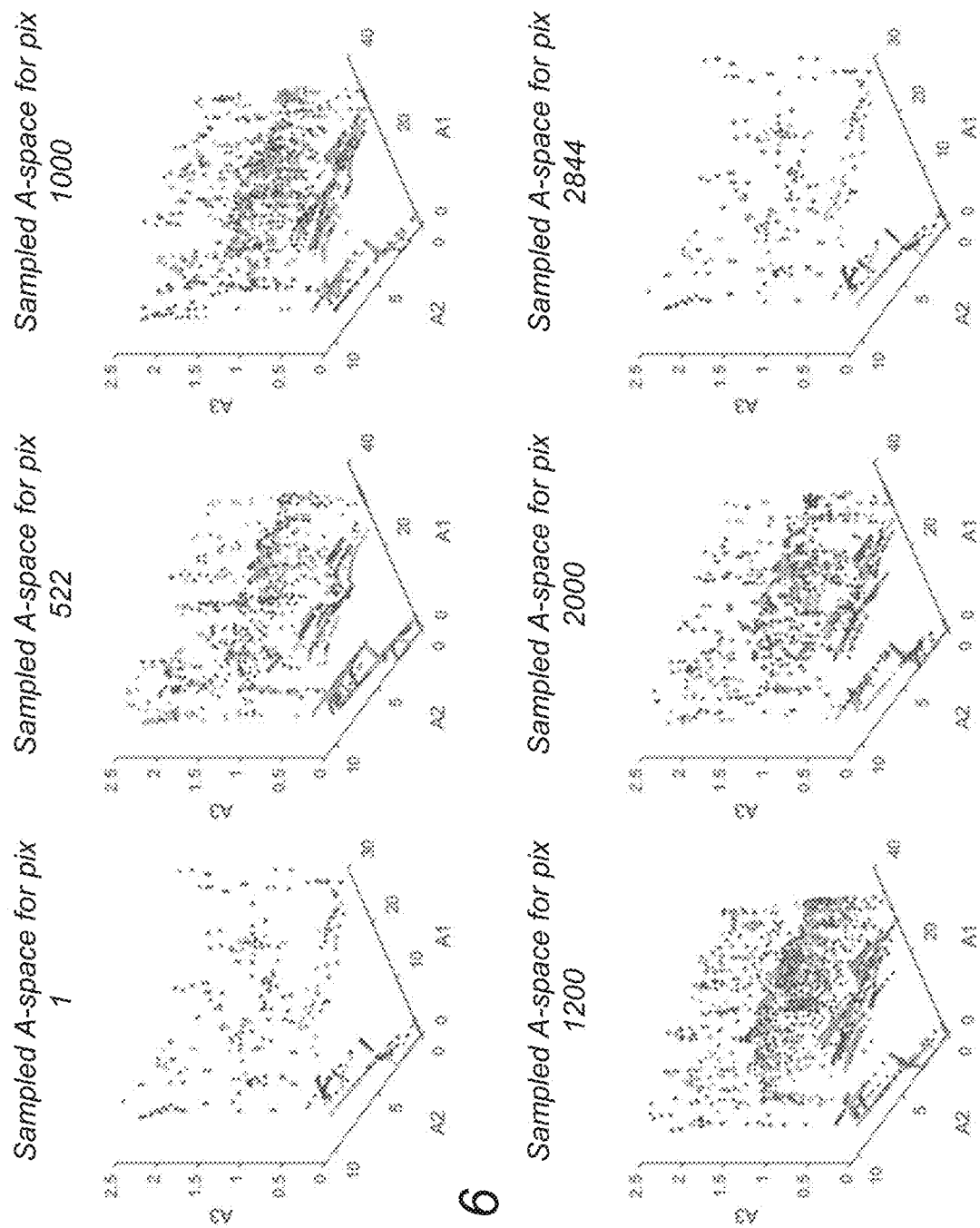
FIG. 6 are schematic diagrams illustrating an example of how the space of material pathlengths may be sampled using the phantom.

In the particular example of FIG. 6, A1 denotes pathlength in cm of material 1 (the large cylinder in the middle, mimicking soft tissue, and every second medium sized cylinder). A2 is corresponding for PVC and A3 is the lengths through the smallest cylinders. This plot shows illustrative pathlengths achieved for a phantom with middle cylinder being 25 cm in cm, having 20 medium and small sized cylinders placed around it. Pix 1 is the left-most detector element and pix 2844 is the right-most elements. Due to symmetry, they sample A-space (material combination space) similarly (in this case the phantom was first placed in iso-center and then stepped out by 2 cm 10 times, to ensure part of the phantom fell outside the field-of-view).

Some of the Main Benefits/Features of the Invention May Include One or More of the Following:

Overcoming the excessive combinatorics of using step-wedge like phantoms, resulting in either very large calibration phantoms or very complicated movements of the calibration during the calibration procedure.

Overcoming the sparse sampling of material combinations when the smaller objects are placed in the interior of the larger object.

Overcoming the need for highly accurate placement of the calibration phantom; instead the exact locations of the phantom rods are determined, e.g. from the actual data that is generated by means of a fitting procedure. If the phantom is aligned with the scan axis, the cross section of the phantom will consist of circles touching each other. If the phantom is slanted, they will be ellipses. These shapes are easily identified in the image (for example by a modified Hough transform) on in the sinogram; their exact location can be determined as function of a few parameters (skew and tilt angles, center position, rotation).

Given the phantom location, the pathlengths through each of the material for each gantry angle and detector element position can be analytically determined. This material combination is then mapped to the detector response yielding the necessary calibration data. This can be done for any type of geometric objects.

The phantom and method may optionally also handle scattered x-rays better. If scatter is not compensated for prior to determining the calibration table, the result of scatter will at the very least be averaged over different angles (smoothing any possible angular dependency) and also be representative of a real scatter profile (as the suggested rod phantom will mimic a patient better than a step wedge). If one wants to acquire the calibration data net of scatter, the scatter profile can be estimated by applying narrow collimation to the x-ray beam and examine the response of detectors not directly exposed to primary x-rays.

In a particular example, a calibration procedure based on the novel calibration phantom may be using the following features and actions:
1. Place the phantom in the beam path.
2. Turn-on the x-ray source and begin calibration sequence based on controlled movement of the phantom.
3. Store projection data.
4. Determine pathlengths through relevant calibration phantom materials for each projection, at least partly based on acquired projection data.
5. Generate a mapping of material pathlength combinations and detector response for each detector element (thereby providing a representative calibration).
6. Optionally, use the mapping for artefact-free tomographic image reconstruction.

In a particular example, the detector response may at least partly be represented by the projection data, such as counts in energy bins, also referred to as photon count information.

Optionally, the step of determining path lengths may involve generating an image of the phantom or at least part thereof, at least partly based on acquired projection data, such as photon count information, and determining the path lengths from the generated image. Ring artefacts may be present in such an image, and although these artefacts are normally not tolerated in a clinical image of a patient, they may be acceptable for the purpose of determining geometric objects of the phantom from the image and determining path lengths for each of the considered materials of the phantom.

Figure 7:
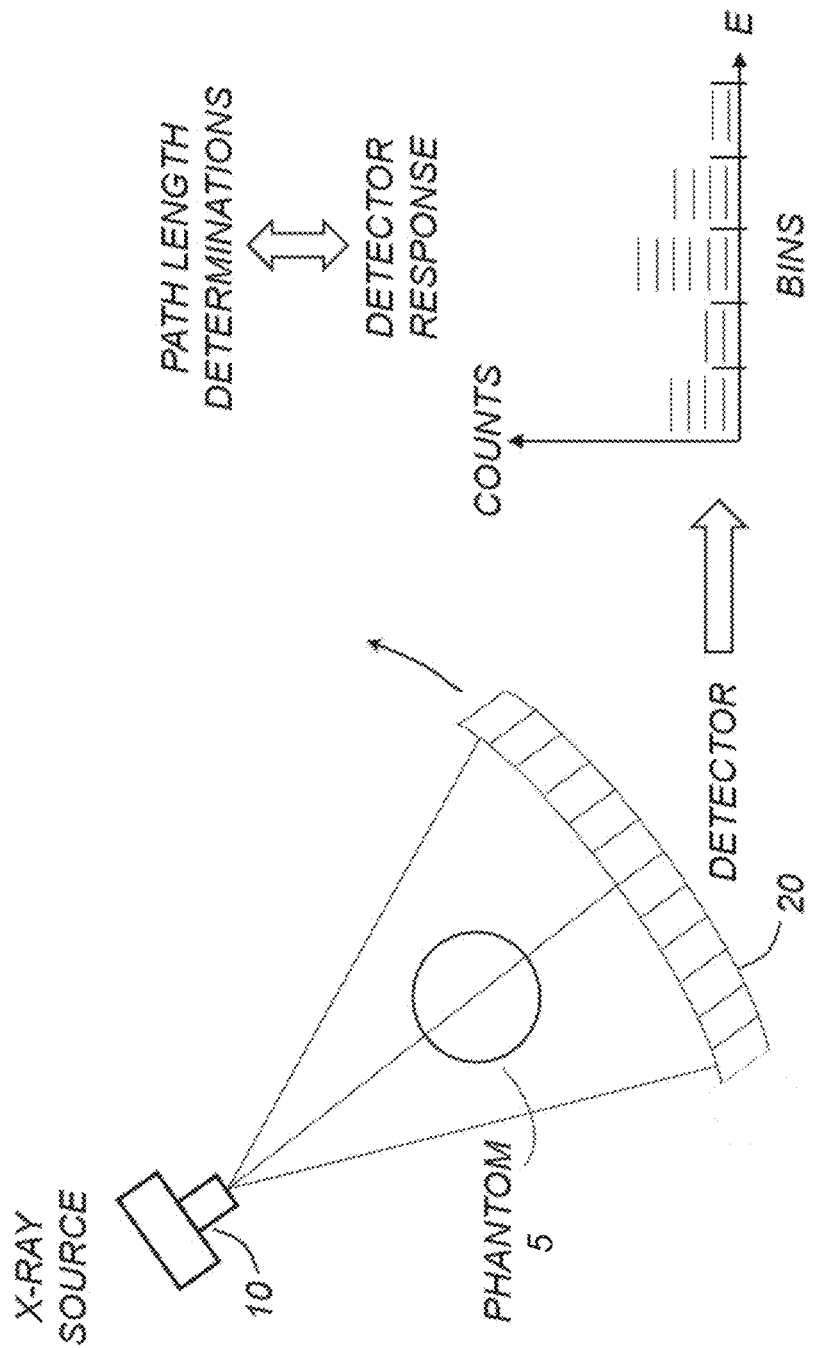
FIG. 7 is a schematic diagram illustrating an example of relevant parts of an x-ray imaging system according to an embodiment.

FIG. 7 is a schematic diagram illustrating an example of relevant parts of an x-ray imaging system such as a CT system with a photon-counting multi-bin x-ray detector. The x-ray source and detector may be mounted in a gantry that rotates around the imaged object to enable a set of different projections at different view angles during each rotation. The output of the x-ray detector includes photon-count information organized in different energy bins. Pathlengths through each of the relevant calibration phantom materials can be determined for each projection and mapped to the detector response for each considered detector element.

Figure 8B:
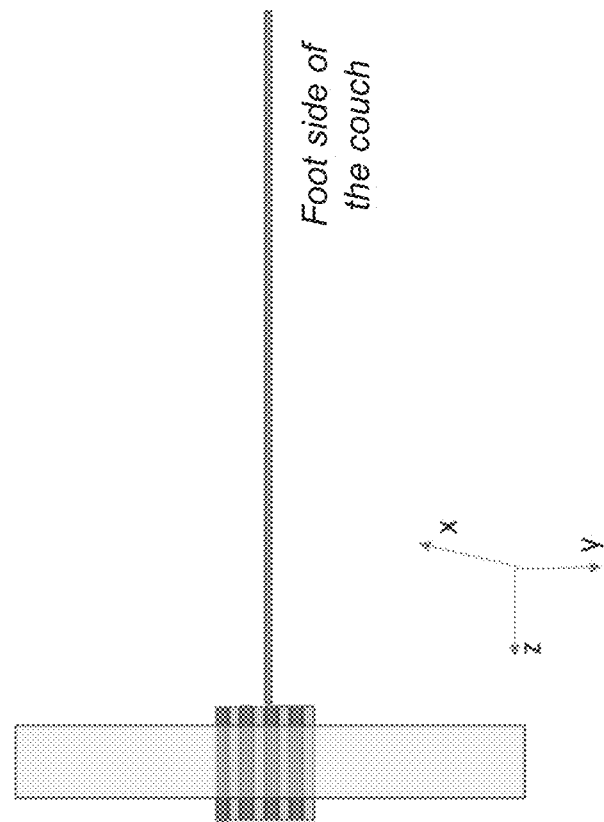
FIGS. 8A-B are schematic diagrams illustrating an example of phantom placement according to an embodiment.
Figure 8A:
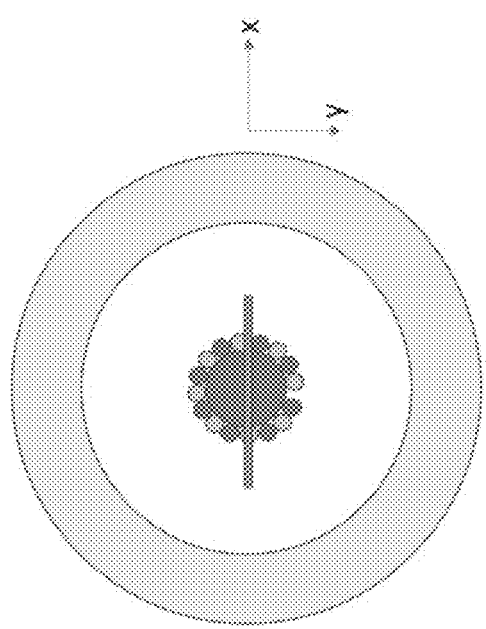

In the following, a more detailed step-by-step description of a non-limiting example of a calibration procedure will be given:

Manually place the calibration phantom on a holder extending from the tip of the patient couch placing the phantom in the beam path (see FIG. 8A and FIG. 8B).

It is a benefit but not a necessity if the main axis of the phantom is (roughly) parallel to the z-axis. Since the phantom is homogenous in the z-direction, the method is insensitive to small shifts in z. A perfect alignment with the z-axis will ensure that all detector rows in a multi-slice system see identical material combinations and the cross section of each rod is a circle.

X-ray source is turned on and an automated calibration sequence commences, comprising either:

A smooth continuous movement of the calibration phantom within and at least partly exceeding to the field-of-view; or A stepwise movement of the phantom covering and at least partly exceeding the field-of-view. Between each step the phantom is stationary and the gantry rotates a number of revolutions, collecting projection data from a set of angles. The number of revolutions is determined based on desired statistical error in the measurement data.

All projection data is stored (for example counts in the energy bins, possibly after corrections for scatter and pile-up and also possibly log-normalized)

For each of a number of positions of the phantom (steps or continuous movement up-down and/or left right toward the periphery of the field of view), the actual pathlength through the different materials of the calibration phantom is determined, e.g. in the following manner:

Make a reconstructed image of the phantom at least partly based on the projection data. Extract the parametric representation of the salient features of the phantom constituents (ellipsoid center, large and minor axes etc), utilizing for example a transform similar to the Hough transform on the image of the phantom after edge extraction (see FIGS. 9A-C).

Having determined the parametric representation, the geometry and location of the phantom is uniquely known. The pathlength through different materials seen by each detector element can now be determined analytically using formulae for the intersection of line segments with circles (or ellipsoids), or any other geometric forms used for the phantom, each line segment being uniquely determined by its starting point (the x-ray focal spot) and its end point, the known location of each detector element for given gantry rotation angle.

Use the detector-element specific mapping of pathlengths of different materials to registered counts for subsequent artefact-free image formation, possibly based on the method of material basis decomposition (Alvarez, 2011). It is also possible to use the resulting mapping to fit a forward model to the projection data (valid also for unseen material combinations) following the method proposed by Ehn et al (2016). For the accurate fitting of such models, it is beneficial not to sample the material space sparsely, as would be the case with interiorly placed cylinders of material base 2 (for example PVC) and/or 3 (for example iodine).

Figures 9A, 9B, 9C:
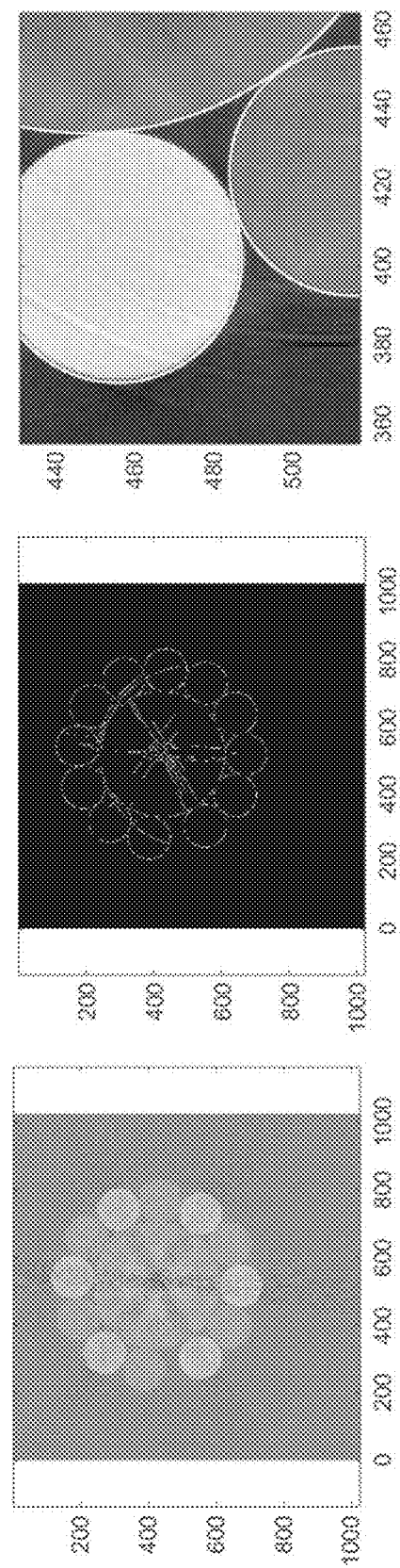
FIG. 9A is a schematic diagram illustrating an example of initial reconstruction of a two-material phantom (on a non-calibrated system resulting in the image containing ring artefacts).
FIG. 9B is a schematic diagram illustrating an example of a result of edge extraction.
FIG. 9C is a schematic diagram illustrating an example of a close-up of the result of the Hough transform for identifying the locations of the ellipsoids (the cross sections through the cylinders will be ellipsoids).

FIG. 9A is a schematic diagram illustrating an example of initial reconstruction of a two-material phantom (on a non-calibrated system resulting in the image containing ring artefacts).

FIG. 9B is a schematic diagram illustrating an example of a result of edge extraction.

FIG. 9C is a schematic diagram illustrating an example of a close-up of the result of the Hough transform for identifying the locations of the ellipsoids (the cross sections through the cylinders will be ellipsoids).

Figure 10:
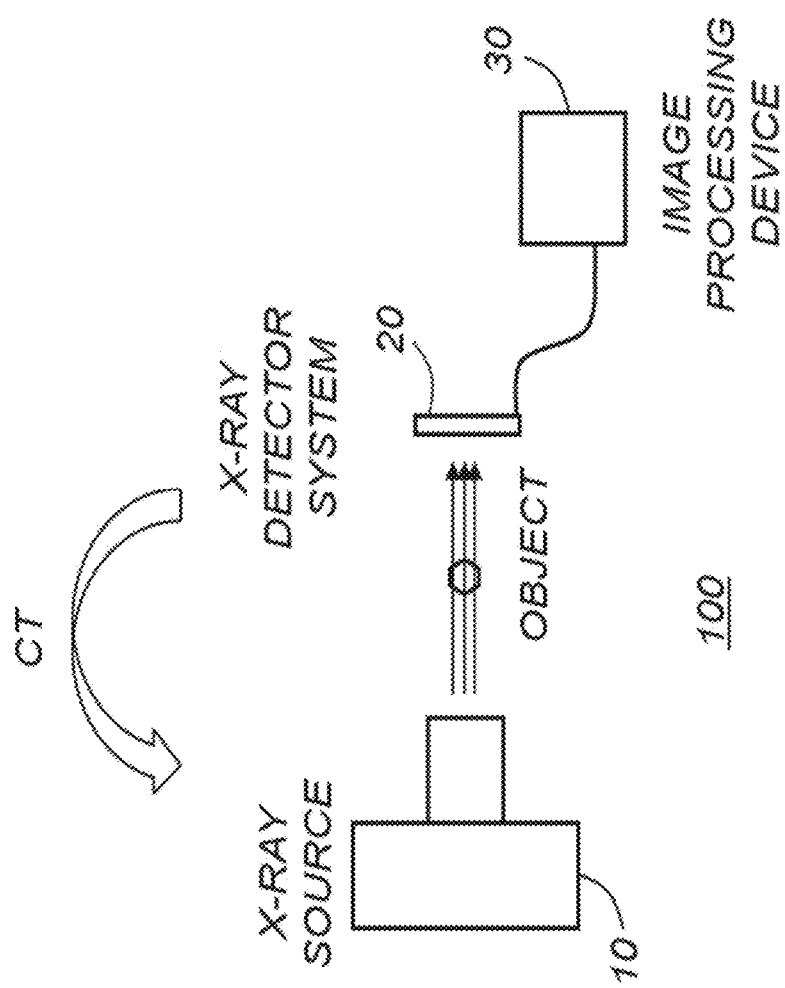
FIG. 10 is a schematic diagram illustrating an example of an overall x-ray imaging system according to an embodiment.

For completeness, it may be useful to provide a brief overview of an illustrative example of an overall x-ray imaging system, with reference to FIG. 10, which is a schematic diagram illustrating an example of an overall x-ray imaging system according to an embodiment.

In this non-limiting example, the x-ray imaging system 100 basically comprises an x-ray source 10, an x-ray detector system 20 and an associated image processing device 30.

The x-ray source emits x-rays, which pass through a subject or object to be imaged and are then registered by the x-ray detector system. Since some materials absorb a larger fraction of the x-rays than others, an image may be formed of the subject or object.

In general, the x-ray detector system 20 is configured for registering radiation from the x-ray source 10 that may have been focused by optional x-ray optics and passed an object or subject or part thereof. The x-ray detector system 20 is connectable to the image processing device 30 via suitable analog processing and read-out electronics (which may be integrated in the x-ray detector system 20) to enable image processing, such as basis material decomposition and/or image reconstruction by the image processing device 30.

An example of a commonly used x-ray imaging system is a Computed Tomography (CT) system, which may include an x-ray source that produces a fan or cone beam of x-rays and an opposing x-ray detector system for registering the fraction of x-rays that are transmitted through a patient or object. The x-ray source and detector system are normally mounted in a gantry that rotates around the imaged object.

Accordingly, the x-ray source 10 and the x-ray detector system 20 illustrated in FIG. 7 and FIG. 10 may thus be arranged as part of a CT system, e.g. mountable in a CT gantry.

In this example, the x-ray detector system 20 is a photon-counting multi-bin detector, and the image processing device 30 may receive photon count information from the x-ray detector 20 as input for basis material decomposition and/or image reconstruction as described herein.

Figure 11:
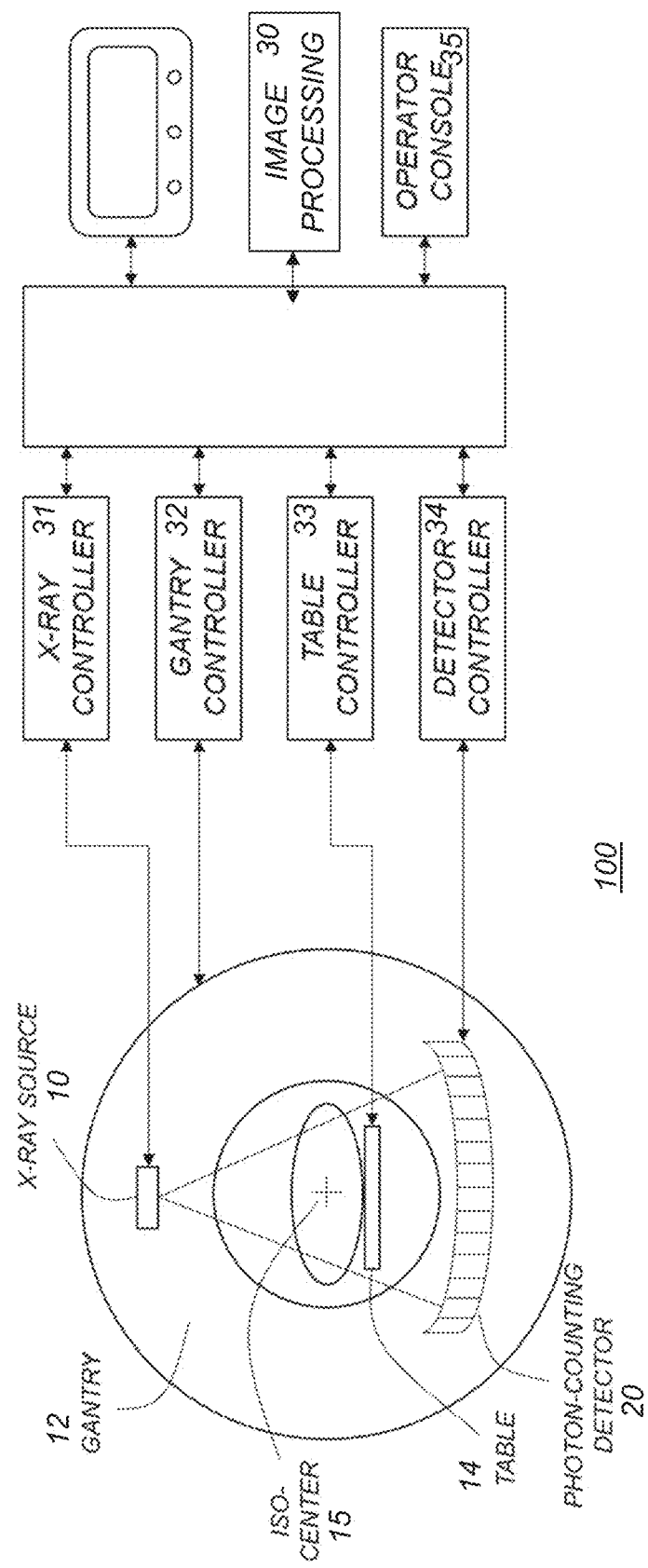
FIG. 11 is a schematic diagram illustrating another example of an overall x-ray imaging system according to an embodiment.

FIG. 11 is a schematic diagram illustrating another example of an overall x-ray imaging system according to an embodiment. In this example, the x-ray imaging system 100 comprises an x-ray source 10, a gantry 12, and a patient table 14, an x-ray detector system 20, an associated image processing device 30, various controllers 31, 32, 33, 34, an operator console 35 and a display.

In this example, the x-ray source 10 and x-ray detector system 20 are mounted in a gantry 12 that rotates with respect to an iso-center 15.

In this non-limiting example, the various controllers include an x-ray controller 31 for controlling the x-ray source, e.g. for switching it on and off, and for controlling the mode of operation such as kV-switched mode. The system 100 also includes a gantry controller 32 and a table controller 33, e.g. for controlling the movements and rotation of the gantry and the table, respectively. There is also a detector controller 34 for controlling the operations of the photon-counting multi-bin detector 20 including read-out of photon count information and other possible detector output.

In this embodiment, also, the x-ray detector system 20 is connectable to the image processing device 30 via suitable analog processing and read-out electronics and analog and/or digital data paths to enable image processing, basis material decomposition and/or image reconstruction by the image processing device 30.

The system 100 may also include an operator console 35 with an associated display for allowing an operator to interact with the system.

It will be appreciated that the methods and devices described herein can be combined and re-arranged in a variety of ways.

For example, specific functions may be implemented in hardware, or in software for execution by suitable processing circuitry, or a combination thereof.

The steps, functions, procedures, modules and/or blocks described herein may be implemented in hardware using any conventional technology, such as semiconductor technology, discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

Figure 12:
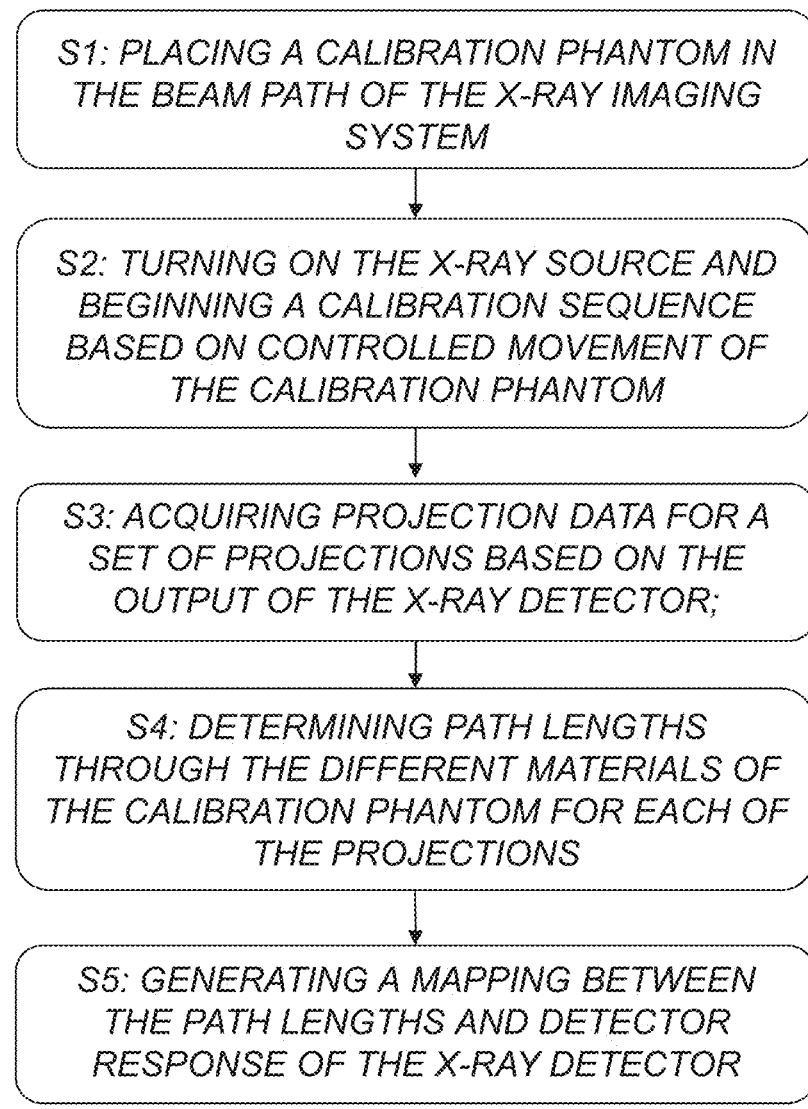
FIG. 12 is a schematic flow diagram illustrating an example of a method for calibration of an x-ray imaging system having an x-ray source and an x-ray detector.

FIG. 12 is a schematic flow diagram illustrating an example of a method for calibration of an x-ray imaging system having an x-ray source and an x-ray detector.

Basically, the method comprises:
S1: placing a calibration phantom of any of the claims 1 to 16 in the beam path of the x-ray imaging system;
S2: turning on the x-ray source and beginning a calibration sequence based on controlled movement of the calibration phantom;
S3: acquiring projection data for a set of projections based on the output of the x-ray detector;
S4: determining path lengths through the different materials of the calibration phantom for each of the projections, at least partly based on acquired projection data; and
S5: generating a mapping between the path lengths and detector response of the x-ray detector.

For example, the mapping may be used for calibrated image reconstruction.

By way of example, the determining step S4 comprises determining the path lengths through each of the first, second and third material of the calibration phantom for each of a number of rotation angles and each of a number of detector elements of the x-ray detector.

In a particular example, the x-ray detector is a photon-counting multi-bin x-ray detector, and the generating step S5 comprises determining a detector-element specific mapping of path lengths of the different materials to corresponding registered photon counts of the photon-counting multi-bin x-ray detector.

By way of example, the detector response may at least partly be represented by the projection data.

For example, the projection data may include photon count information.

Optionally, the step of determining path lengths may include generating an image of the phantom or at least part thereof at least partly based on acquired projection data, and determining the path lengths from the generated image, e.g. as previously exemplified.

As an example, the x-ray imaging system may be a Photon-Counting Spectral Computed Tomography (PCSCT) system with a photon-counting multi-bin x-ray detector.

Figure 13:
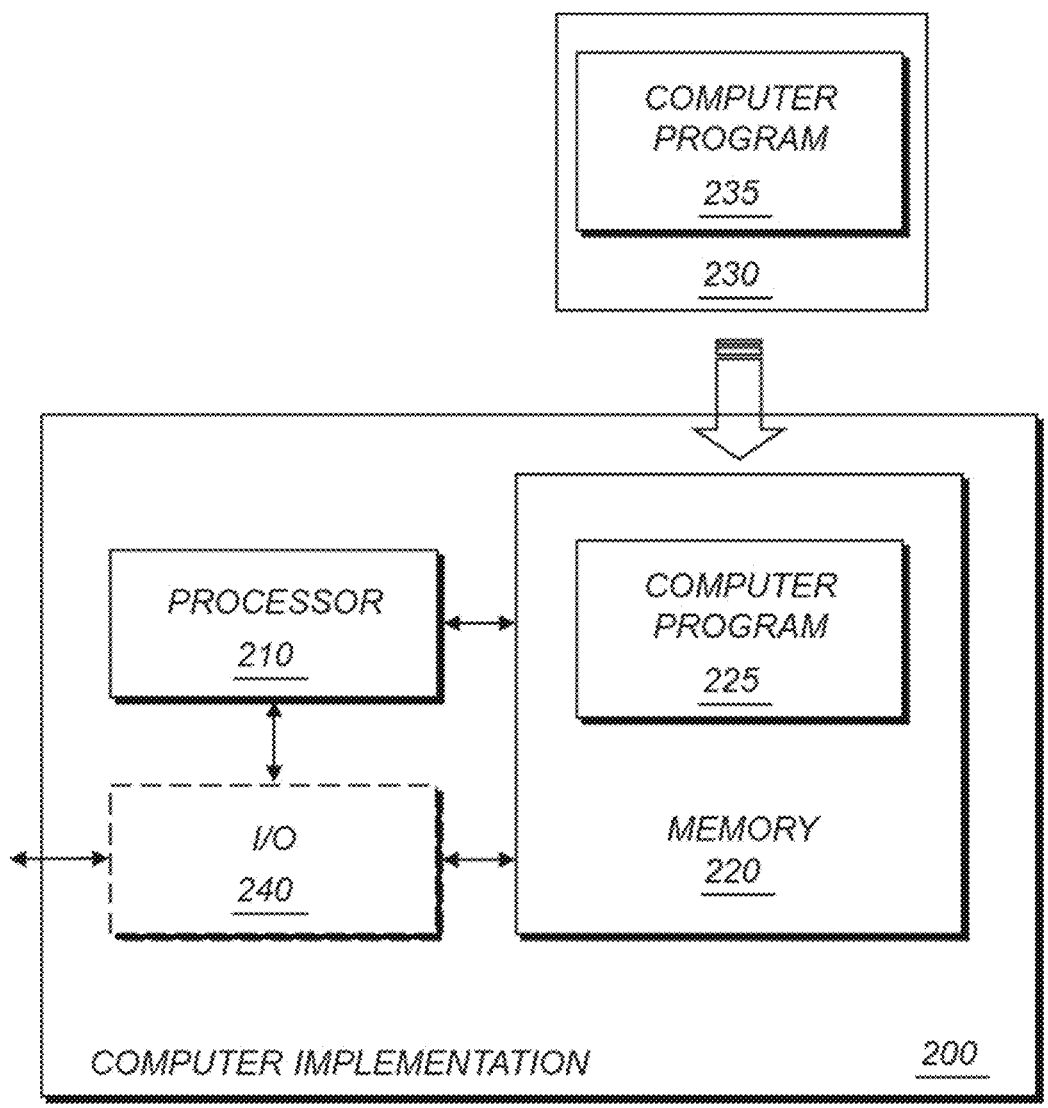
FIG. 13 is a schematic diagram illustrating an example of a computer implementation according to an embodiment.

FIG. 13 is a schematic diagram illustrating an example of a computer implementation according to an embodiment.

In this particular example, the system 200 comprises a processor 210 and a memory 220, the memory comprising instructions executable by the processor, whereby the processor is operative to perform computer-implementable steps and/or actions described herein. The instructions are typically organized as a computer program 225; 235, which may be preconfigured in the memory 220 or downloaded from an external memory device 230. Optionally, the system 200 comprises an input/output interface 240 that may be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Method flows or relevant parts thereof may be regarded as computer action flows, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Alternatively, it is possibly to realize the modules predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the invention. In particular, different part solutions in the different embodiments can be combined in other configurations, where technically possible.

REFERENCES

1. Alvarez, Robert E. "Estimator for photon counting energy selective x-ray imaging with multibin pulse height analysis", Med. Phys. 38 (5), May 2011.
2. Ehn, S, Sellerer, T, Mechlem, K, Fehringer, A, Epple, M, Herzen, J, Pfeiffer, F, Noel, P B, "Basis material decomposition in spectral CT using a semi-empirical, polychromatic adaption of the Beer-Lambert model", Phys. Med. Biol. 62 (2017)

The invention claimed is:

1. A calibration phantom for an x-ray imaging system having an x-ray source and an x-ray detector,
wherein said calibration phantom comprises a combination of geometric objects of at least three different types and/or compositions including:
a first object located in the middle, comprising a first material;
a plurality of second objects arranged around the periphery of the first object, at least a subset of the second objects comprising a second material different than the first material, wherein the first object is relatively larger than the second objects;
a plurality of third objects arranged around the periphery of the first object and/or around the periphery of at least a subset of the second objects, at least a subset of the third objects comprising a third material different than the first material and the second material, wherein the third objects are relatively smaller than the second objects.

2. The calibration phantom of claim 1, wherein at least a subset of the third objects are arranged around the periphery of the first object in-between at least a subset of the second objects.

3. The calibration phantom of claim 1, wherein the first object, the second objects and the third objects are elongated objects extending in a direction substantially perpendicular to the intended x-ray direction and/or extending in the scanning direction.

4. The calibration phantom of claim 1, wherein the first object, the second objects and the third objects include at least one of cylinders, cuboids, and prisms.

5. The calibration phantom of claim 1, wherein the first object is a middle cylinder, the second objects are medium-sized cylinders spaced around the periphery of the middle cylinder, and the third objects are smaller cylinders arranged around the periphery of the middle cylinder and/or around the periphery of at least a subset of the medium-sized cylinders.

6. The calibration phantom of claim 5, wherein at least a subset of the smaller cylinders are arranged around the periphery of the middle cylinder in spacings in-between at least a subset of the medium-sized cylinders.

7. The calibration phantom of claim 5, wherein the middle cylinder has a larger diameter than the medium-sized cylinders, and the medium-sized cylinders have a larger diameter than the smaller cylinders.

8. The calibration phantom of claim 1, wherein the plurality of second objects are all of the same second material.

9. The calibration phantom of claim 1, wherein the plurality of second objects includes at least two types of second objects, of different materials and/or different sizes.

10. The calibration phantom of claim 9, wherein a first subset of the second objects are made of the second different material and a second subset of the second objects are made of the first material.

11. The calibration phantom of claim 1, wherein the size and number of the second objects are selected to achieve a snug fit of the second objects around the periphery of the first object.

12. The calibration phantom of claim 1, wherein the first material mimics soft human tissue, and the second material has a higher attenuation than the first material.

13. The calibration phantom of claim 1, wherein the first material mimics soft human tissue, the second material mimics bone, and the third material mimics a contrast agent.

14. The calibration phantom of claim 1, wherein the first material comprises polyethylene (PE), and the second material comprises poly-vinyl-chloride (PVC) or other plastic or resin.

15. The calibration phantom of claim 1, wherein the calibration phantom is intended for use in a Computed Tomography (CT) system with a photon-counting multi-bin x-ray detector to enable calibration for material basis decomposition.

16. The calibration phantom of claim 15, wherein the calibration phantom is intended for use in the CT system to enable calibration for accurate material basis decomposition based on mapping between i) path length determinations through each of the first, second and third materials for each of a number of rotation angles of the CT system and each of a number of detector elements of the x-ray detector and ii) corresponding detector responses of the photon-counting multi-bin x-ray detector.

17. A method for calibration of an x-ray imaging system having an x-ray source and an x-ray detector, said method comprising:
placing a calibration phantom of claim 1 in the beam path of the x-ray imaging system;
turning on the x-ray source and beginning a calibration sequence based on controlled movement of the calibration phantom;
acquiring projection data for a set of projections based on the output of the x-ray detector;
determining path lengths through the different materials of the calibration phantom for each of the projections, at least partly based on acquired projection data; and
generating a mapping between the path lengths and detector response of the x-ray detector.

18. The method of claim 17, wherein the mapping is used for calibrated image reconstruction.

19. The method of claim 17, wherein the determining step comprises determining the path lengths through each of the first, second and third material of the calibration phantom for each of a number of rotation angles and each of a number of detector elements of the x-ray detector.

20. The method of claim 17, wherein the x-ray detector is a photon-counting multi-bin x-ray detector, and the generating step comprises determining a detector-element specific mapping of path lengths of the different materials to corresponding registered photon counts of the photon-counting multi-bin x-ray detector.

21. The method of claim 17, wherein the detector response is at least partly represented by the projection data.

22. The method of claim 17, wherein the projection data includes photon count information.

23. The method of claim 17, wherein the step of determining path lengths includes generating an image of the phantom or at least part thereof at least partly based on acquired projection data, and determining the path lengths from the generated image.

24. The method of claim 17, wherein the x-ray imaging system is a Photon-Counting Spectral Computed Tomography (PCSCT) system with a photon-counting multi-bin x-ray detector.

* * * * *